Figure 1A:
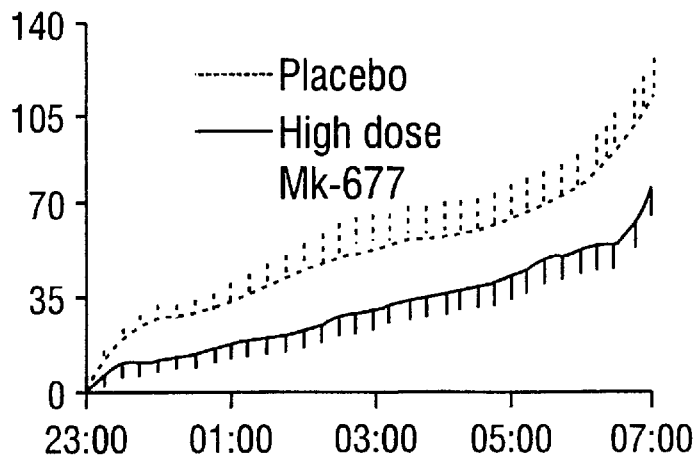

United States Patent [19]
Van Cauter et al.

[11] Patent Number: 6,071,926
[45] Date of Patent: Jun. 6, 2000

[54] SLEEP QUALITY IMPROVEMENT USING A GROWTH HORMONE SECRETAGOGUE

[75] Inventors: Eve Van Cauter, Chicago, Ill.; Georges Copinschi, Brussels, Belgium

[73] Assignee: Arch Development Corporation, Chicago, Ill.

[21] Appl. No.: 09/125,562

[22] PCT Filed: May 22, 1997

[86] PCT No.: PCT/US97/09188

§ 371 Date: Jun. 15, 1999

§ 102(e) Date: Jun. 15, 1999

[87] PCT Pub. No.: WO97/44042

PCT Pub. Date: Nov. 27, 1997

Related U.S. Application Data

[60] Provisional application No. 60/018,110, May 22, 1996.

[51] Int. Cl.[7] .................................................. A61K 31/445
[52] U.S. Cl. ............................................................ 514/278
[58] Field of Search ...................... 514/323, 278

[56] References Cited

FOREIGN PATENT DOCUMENTS

WO 94/13696  6/1994  WIPO .
WO 97/41879  11/1997  WIPO .

OTHER PUBLICATIONS

Mendelson et al., "The effect of growth hormone administration on human sleep: a dose–response study," *Biological Psychiatry*, 15(4):613–618, 1980.

Obál Jr., et al., "Inhibition of growth hormone–releasing factor suppresses both sleep and growth hormone secretion in the rat," *Brain Research*, 557:149–153, 1991.

*Primary Examiner*—Phyllis G. Spivack
*Attorney, Agent, or Firm*—Pillsbury Madison & Sutro LLP

[57] ABSTRACT

A method for sleep quality is disclosed comprising administering an effective amount of N-[1(R)-[(1,2-dihydro-1-methanesulfonylspiro-(3H-indole-3,4'-piperidin)-1'-yl) carbonyl]-2-(phenylmethoxy)-ethyl]-2-amino-2-methylpropanamide methansulfonate.

12 Claims, 6 Drawing Sheets

SLEEP QUALITY IMPROVEMENT USING A GROWTH HORMONE SECRETAGOGUE

This application claims benefit of U.S. Provisional Application No. 60/018,110 filed May 22, 1996.

The government may own rights in the instant invention pursuant to funding from the National Institutes of Health, under a grant from the National Institute on Aging PO1 AG-11412.

I. FIELD OF THE INVENTION

The present invention relates to the fields of sleep medicine, gerontology and hormonal disorders. In particular, the invention addresses sleep deficiencies that are associated with depressed levels of growth hormone and prolactin.

II. RELATED ART

In young adults, sleep is associated with marked hormonal changes, including increased release of growth hormone (GH) and prolactin (PL). A pulse of GH occurs shortly after sleep onset in association with the first episode of slow-wave sleep (SWS) and often represents 50–100% of the total daily GH output. Sleep onset is associated with a marked increase in PL secretion. PL levels return to low daytime values after morning awakening. There is good evidence to indicate that the nocturnal release of GH and PL contributes to the maintenance and quality of sleep.

In older adults, sleep is disturbed with more awakenings, less SWS and less rapid eye movement (REM) sleep. The most dramatic change is the decrease in SWS, which often represents less than 5% of the sleep period time or, sometimes, disappears entirely in aged individuals. Simultaneously, growth hormone secretion also is markedly decreased, both during sleep and wakefulness. Since sleep-related GH secretion represents the major part of total GH secretion, the reduction or absence of SWS in the elderly plays a major role in contributing to the overall decline in GH secretion. The absence of activation of the GHRH-GH axis in early sleep also may be involved in the fragmentation, shallowness and reduced duration of mid and late sleep. Nocturnal prolactin release also is markedly decreased in old age and this alteration may play an important role in diminished sleep quality.

Conversely, the effects of GH secretion on sleep can be pronounced. Pharmacological doses of GH may increase the duration of rapid-eye movement (REM) sleep in normal subjects In animals, injections of GHRH stimulate REM and non-REM sleep, while inhibition of endogenous GHRH suppresses both sleep and GH secretion. In normal young men, intravenous injections of GHRH may induce marked increases in SW sleep and/or REM sleep, and decreases the amount of wake. These somnogenic effects are dependent on the dosage and timing of administration. The mechanisms by which these hypnotic effects are effected have not been elucidated. Animal data also have suggested involvement of PL in sleep regulation and have indicated that PL may enhance REM sleep.

The implications of reduced GH secretion may be inferred from the findings in untreated GH-deficient adults, ie., subjects who have no GH secretion due to either a congenital defect or pituitary disease. Pathologic states found in such individuals include increased cardiovascular mortality, reduced exercise capacity, reduced muscle strength, subnormal kidney function, defective sweat and temperature regulation, reduced energy expenditure and basal metabolic rate, abnormal thyroid hormone metabolism, increased fat mass, decreased lean body mass, upper body obesity and reduced bone mineral content. All of these abnormal conditions can be partially corrected by expensive GH replacement therapy with synthetic human GH. Most of the aforementioned abnormalities also are present in elderly adults who, incidentally, also have very low levels of GH secretion. Clinical trials with elderly subjects have shown the beneficial effects of GH replacement therapy, similar to that observed in GH-deficient subjects. The implication of reduced PL secretion in old age has not yet been defined.

Unfortunately, treatment with GH injections results in an unphysiological profile of circulating GH levels, i.e., continuously elevated levels as compared to the intermittent pulses that characterize normal GH secretion, and this may be responsible for the development of the undesirable side effects which have been observed in long term treatments, including joint problems (carpal tunnel syndrome), water retention and impaired glucose tolerance.

The older population also is the primary user of hypnotics (Mendelson, 1987), although it is widely accepted that chronic hypnotic use has generally deleterious effects (Prinz, 1995). Commercially available hypnotics, including the benzodiazepines, improve sleep efficiency but do not consistently increase either SW or REM sleep (Gaillard, 1994).

An alternative to these approaches is the development of growth hormone secretagogues or compounds that stimulate release of prolactin. The ability of such secretagogues to provide the same physiologic benefits as natural GH and/or prolactin secretion, however, remains largely untested. Thus, there remains a need for alternatives in therapies in subjects exhibiting reduced GH and prolactin levels.

III. SUMMARY OF THE INVENTION

Therefore, it is an object of the present invention to provide methods of improving the sleep quality in persons having hormonally-related alterations in sleep. More particularly, it is an object of the present invention to identify individuals with age-related sleep disorders and, by increasing the levels of GH and prolactin secretion, improve the sleep quality of these individuals.

In fulfilling these objects, there is provided a method of improving sleep quality comprising the steps of (a) identifying a subject having age-related sleep disorder; and (b) administering to said subject an amount of the drug N-[1 (R){[1,2-dihydro-1-methanesulfonylspiro-( 3H-indole-3,4'-piperidine)-1'yl]carbonyl}-2-(phenylmethoxy)-ethyl]-2-amino-2-methylpropanamide methanesulfonate.

In one embodiment, the subject is at least about forty years old and, in another embodiment, the subject is at least about fifty years old and, in still another embodiment, the subject is at least about sixty years old. In still another embodiment, the subject is experiencing difficulty sleeping. And in still another embodiment, the administration occurs one hour prior to retiring, more preferably within one-half hour of retiring.

In another embodiment, the effective amount of the drug is 1.0–50.0 grams. In yet other embodiments, the effective amount of the drug is 5.0 mg., 10.0 mg. or 25.0 mg. The dosing preferably is oral.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

IV. BRIEF DESCRIPTION OF THE DRAWINGS

Figure 1B:
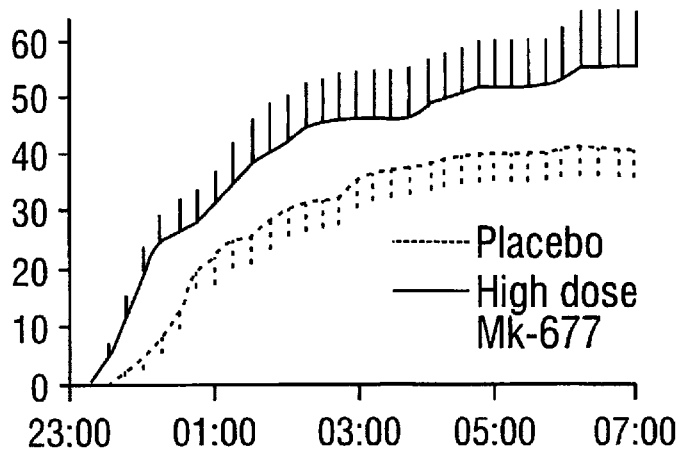
Figure 1C:
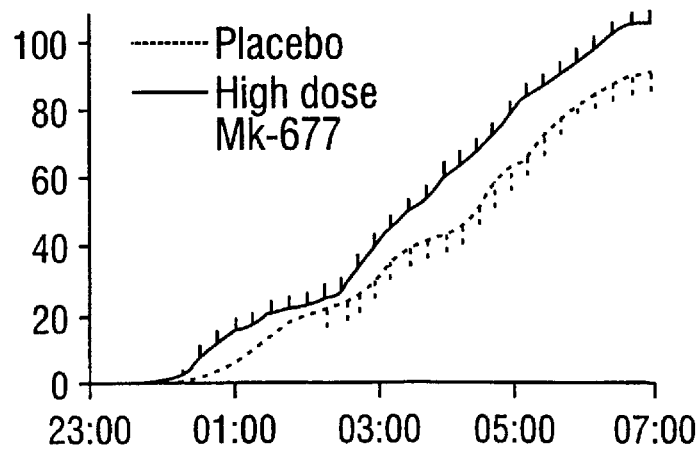

The following drawings form part of the present specification and are included to further demonstrate certain aspects of the present invention. The invention may be better understood by reference to one or more of these drawings in combination with the detailed description of specific embodiments presented herein:

FIGS. 1A–C: Mean and SEM for cumulative minutes of wake (FIG. 1A), stage IV (FIG. 1B) and REM (FIG. 1C) in the eight young patients after 7 days of treatment with placebo (dashed lines) or 25 mg of the drug (solid lines).

Figure 2A:
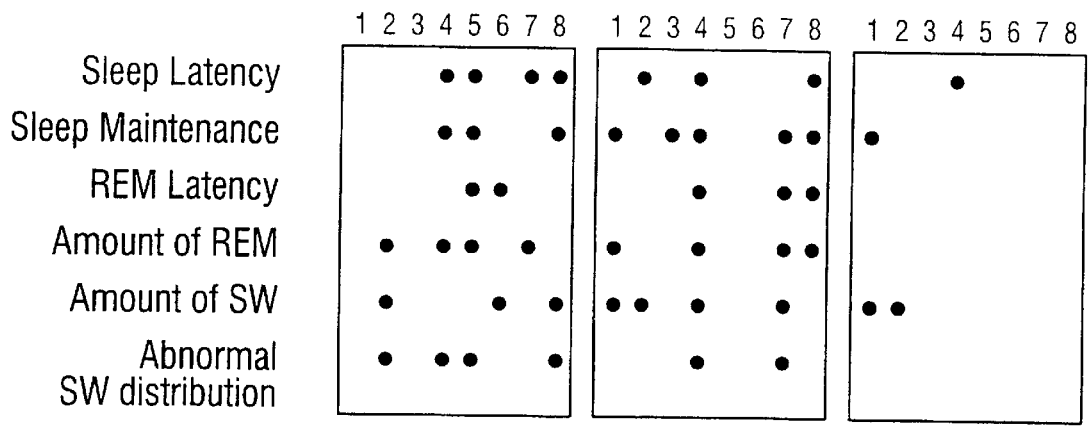
Figure 2B:
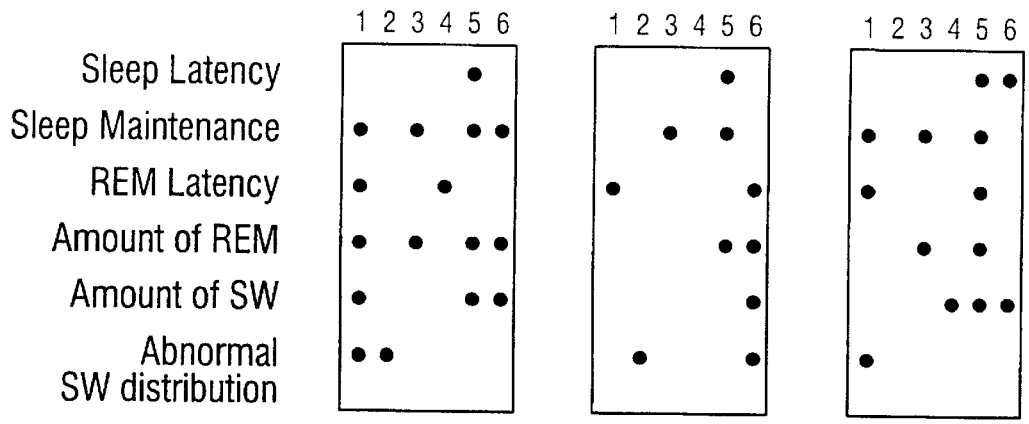
Figure 2C:
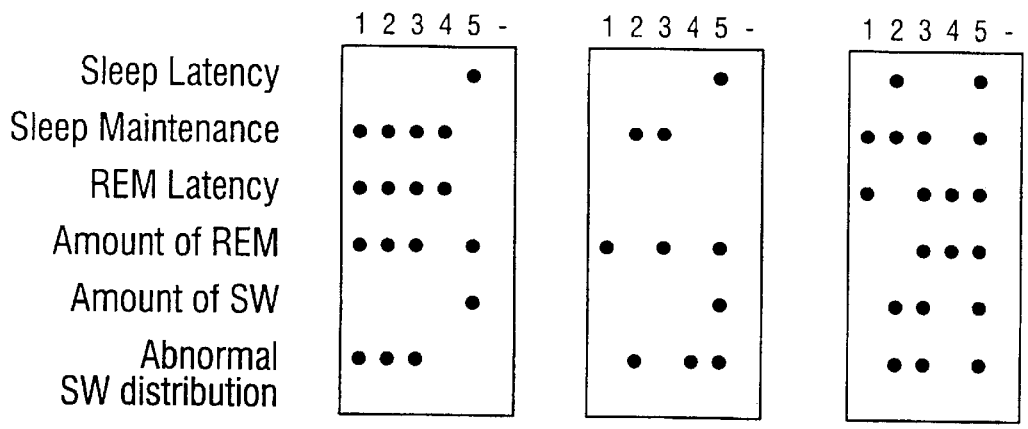

FIGS. 2A–C: Schematic representation of sleep quality in individual nights in young subjects during the night with blood sampling (FIG. 2A) and in older subjects during the nights without and with blood sampling (FIG. 2B and 2C). Closed symbols denote a deviation from normal sleep for each of the criteria. Criteria are: Sleep latency >45 min; Sleep maintenance <85% (FIG. 2A), <80% (FIG. 2B and 2C); REM Latency <40 min or >100 min; Amount of REM <90 min (FIG. 2A), <60 min (FIG. 2B and 2C); Amount of SW <75 min (FIG. 2A), <60 min (FIG. 2B), <45 min (FIG. 2C); Abnormal SW distribution. Left panel=Placebo; Middle panel=low dose; Right panel=high dose.

Figure 3A:
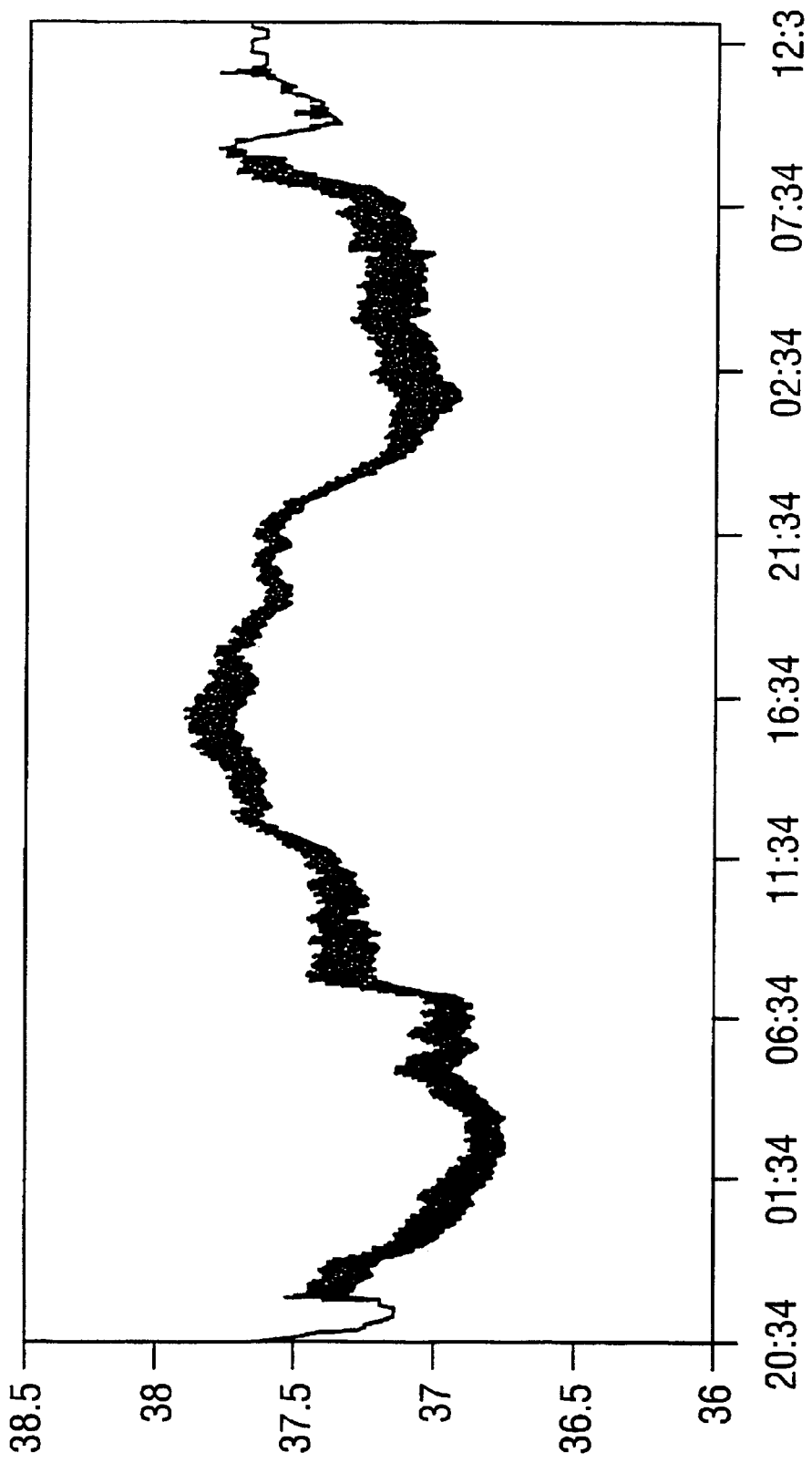
Figure 3B:
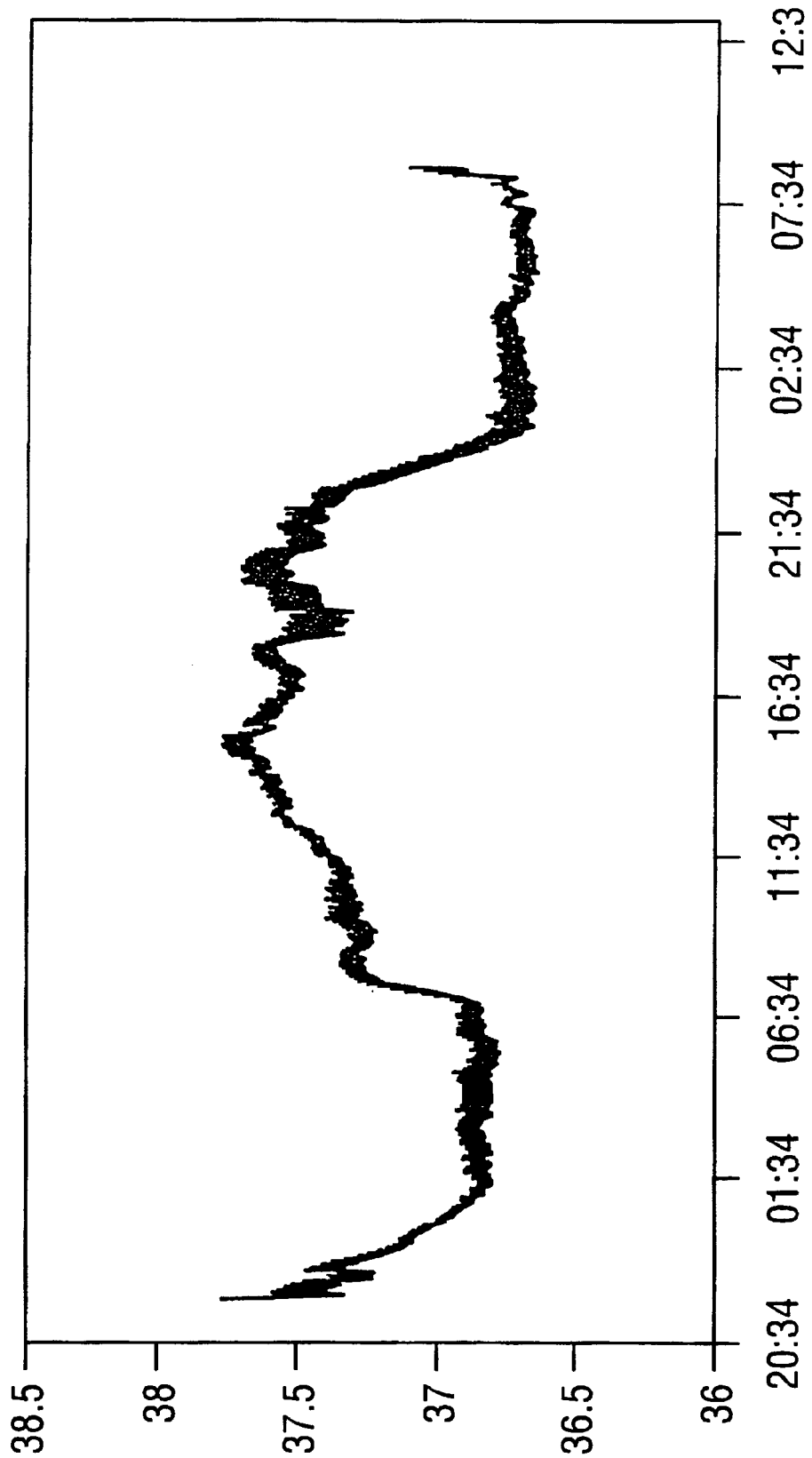
Figure 3C:
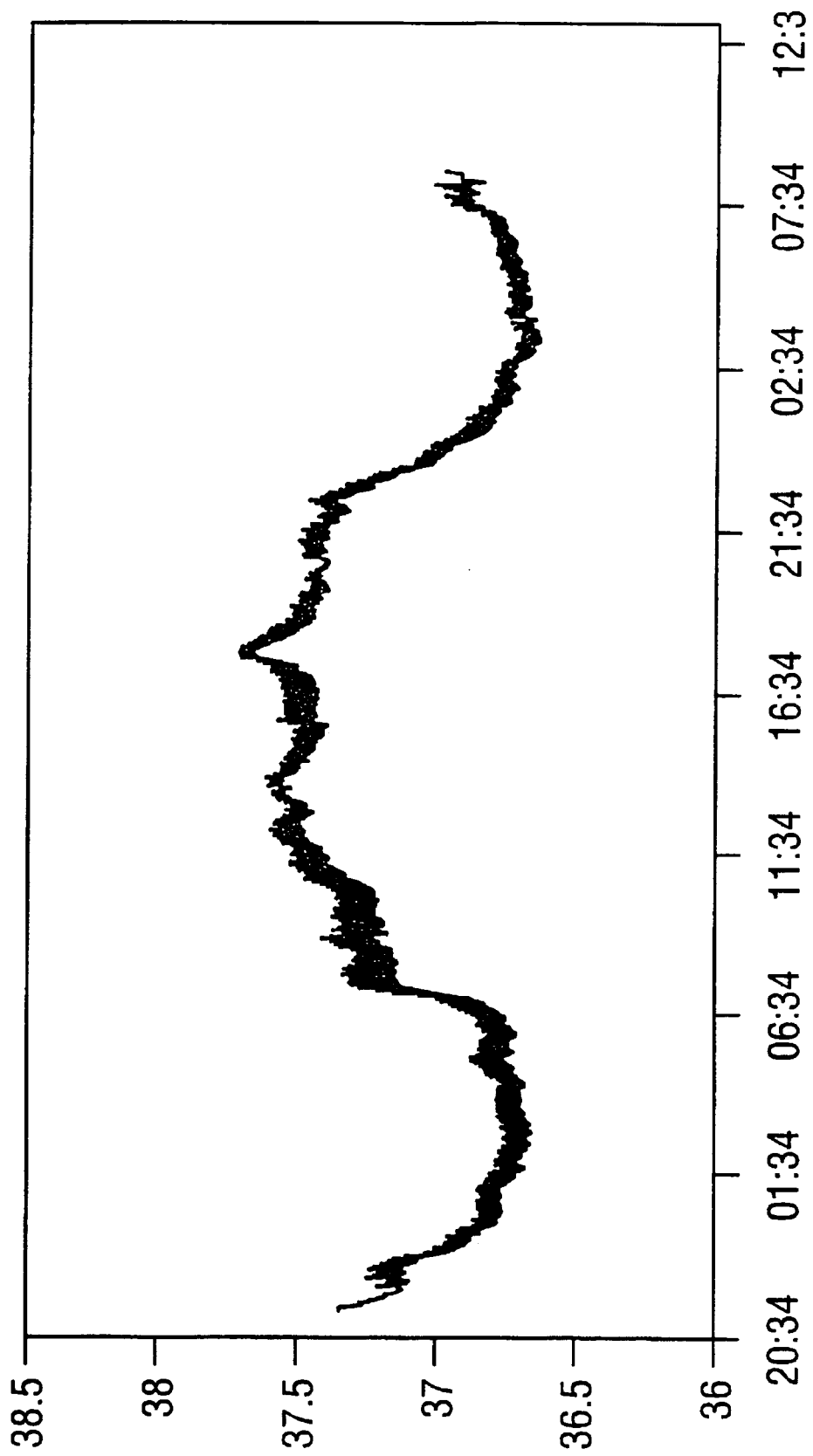

FIGS. 3A–C: Schematic representation of sleep quality in older subjects. FIG. 3A shows mean temperature profiles—baselines, FIG. 3B shows mean temperature profiles—end of period I, and FIG. 3C shows mean temperature profiles—end of period II.

Figure 4:
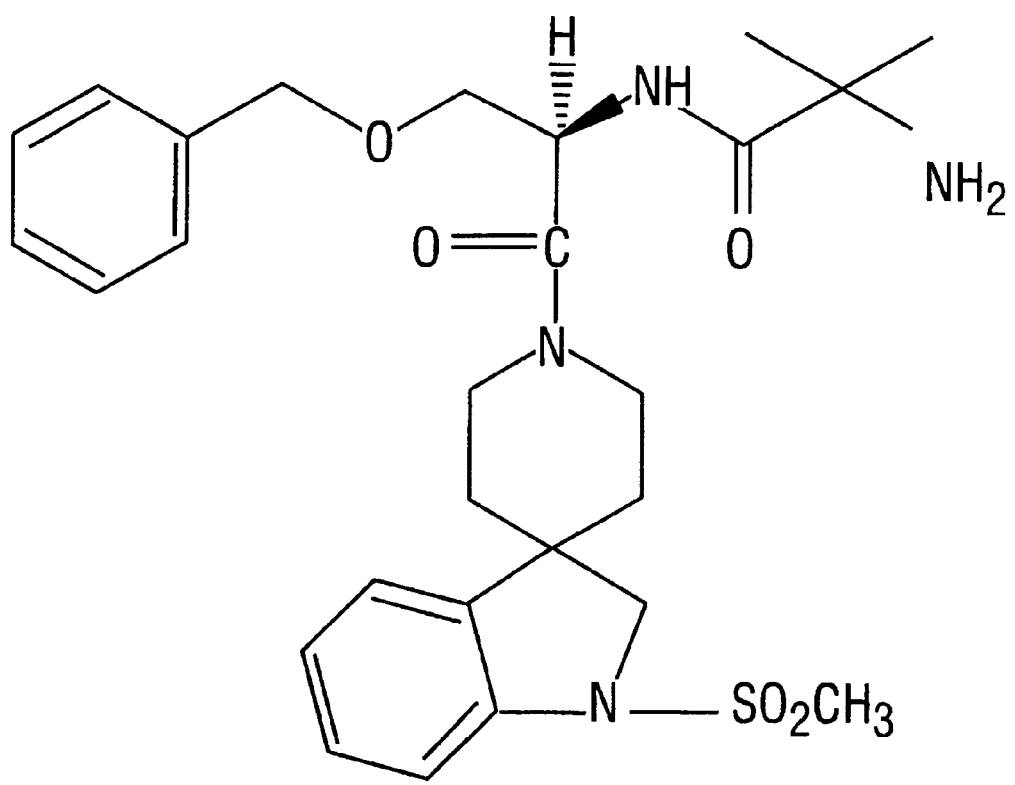

FIG. 4: Illustration of N-[1(R){[1,2-dihydro-1-methanesulfonylspiro-(3H-indole-3,4'-piperidine)-1'yl] carbonyl}-2-(phenylmethoxy)-ethyl]-2-amino-2-methylpropanamide methanesulfonate.

V. DETAILED DESCRIPTION OF THE INVENTION

A. Growth Hormone and Sleep

Early human studies showed the existence of a consistent temporal association between GH secretion and the first SWS period (Sassin, Parker et al. 1969). It later was demonstrated that pulses of GH secretion which occur in late sleep also are preferentially associated with SWS stages (Golstein, Van Cauter et al. 1983). From pulse-by-pulse analysis of nocturnal profiles of GH secretory rate, it has been shown that approximately 70% of GH pulses during sleep are associated with the amount of SWS occurring during the phase (Van Cauter, Kerkhofs et al. 1991). Other studies have reported negative findings, however, suggesting that the relationship between SWS and GH hormone release may be coincidental (Born, Muth et al. 1988; Jarret, Greenhouse et al. 1990; McCracken, Poland et al. 1991; Steiger, Herth et al. 1987). Nonetheless, it has been suggested that a relationship may exist between sleep and GH release and, therefore, that common regulatory mechanisms exist (Obál, Payne et al. 1991a; Obál, Payne et al. 1991b). It is hypothesized that the stimulatory effects of SWS on GH secretion are mediated by GHRH release.

A number of rodent studies have indicated that the hypothalamic factor growth-hormone releasing hormone (GHRH), which controls the release of GH from the pituitary, may be involved in the modulation of sleep. Indeed, intracerebroventricular injections of GBRH in rats and rabbits increase both REM and non-REM sleep (Obál, Alfodi et al. 1988; Ehlers, Reed et al. 1986). Inhibition of endogenous GHRH, either by administration of competitive antagonist or by immunoneutralization, inhibits sleep (Obál, Payne et al. 1991a; Obál, Payne et al. 1991b).

In addition to the foregoing, there also are a number of other findings that indicate that GH secretion may be involved in the maintenance and quality of human sleep. While intravenous administration of synthetic GHRH during the daytime does not modify sleep in normal young men (Garry, Roussel et al. 1985), it has been demonstrated that GHRH administration during sleep may decrease the amount of wake time and increase SWS (Kerkhofs, Van Cauter et al. 1992). In addition, four consecutive GHRH injections at 10 pm, 11 pm, 12 am and 1 am to normal, young males also showed improved sleep (Steiger, Guldner et al. 1991). Pharmacological doses of GH may increase the duration of rapid-eye movement (REM) sleep in normal subjects (Mendelson et al., 1980).

In normal young men, there is evidence of a temporal relationship between sleep and nocturnal GH secretion (Takhashi et al., 1968). The major secretory episode of GH over the 24-hour span is a pulse which occurs shortly after sleep onset and is consistently associated with the first phase of slow-wave (SW) sleep (SW sleep=stages III and IV). In a study where blood was sampled at 30-sec intervals, maximal GH secretion was found to occur within minutes of the onset of SW sleep (Holl et al., 1991). In another study, a pulse-by-pulse analysis of GH secretory profiles has shown that the amount of GH secreted during sleep is closely related to the duration of SW stages, and that interruptions of SW sleep are frequently associated with concomitant interruptions in GH secretion (Van Cauter et al., 1992).

Age-related decreases in GH secretion have been well documented in both men and women (Finkelstein, Roffwarg et al. 1972; Ho, Evans et al. 1987; Iranmanesh, Lizarralde et al. 1991; Prinz, Weitzman et al. 1983, van Coevorden, Mockel et al. 1991; Vermeulen 1987). The mechanisms underlying reduced GH secretion in the aged have not been completely elucidated. A decreased responsiveness to stimulation by exogenous GHRH has clearly been demonstrated in older adults of both sexes (Lang, Schernthaner et al. 1987; Shibasaki, Shizume et al. 1984). Though still controversial, adults treated with synthetic GH report an overall improvement in the quality of life, including higher energy levels and better mood (Degerblad, Almkvist et al. 1990; McCauley 1989).

In the course of aging, somatotropic activity and sleep quality are both markedly altered (Van Coevorden et al., 1991; Copinschi & Van Cauter, 1995). Interestingly, the age-related decrease in GH output occurs in early adulthood, approximately at the same time as the decline in amount of SW sleep. The putative existence of common mechanisms underlying sleep and GH regulation raises the possibility that the age-related alterations in sleep quality, as well as the relative GH deficiency of older adults, could both benefit from a common treatment.

B. Prolactin and Sleep

Under normal conditions, the 24-hour profile of PL levels follows a bimodal pattern, with minimal concentrations around noon, an afternoon phase of slightly augmented secretion, and a major nocturnal elevation starting shortly after sleep onset and culminating around mid-sleep. In male adults, the range of this diurnal variation corresponds to an average increase of more than 250% above the minimum noon level.

Studies of PL levels during daytime naps or after shifts of the normal sleep period have consistently demonstrated increased PL secretion associated with sleep onset (Van Cauter & Refetoff, 1985). Based on pharmacological studies, dopaminergic as well as serotoninergic mechanisms seem to be implicated in this sleep-related elevation of secretion. Studies involving abrupt shifts of the sleep-wake cycle, during real or simulated "jet lag," also have revealed the existence of a sleep-independent secretory rise (Desir et al., 1982; Van Cauter & Refetoff, 1985; Van Cauter et al., 1988). Under normal conditions, this circadian rise is synchronized with the early part of sleep and both circadian and sleep effects are superimposed.

A number of studies have examined the relationship between sleep stages, i.e., the alternation of REM and non-REM stages, and pulsatile variations of PL. These have shown that PL secretion tends to occur more during SW sleep than during REM sleep and that awakenings interrupting sleep are consistently associated with decreasing PL concentrations. These data indicate that fragmented sleep will generally be associated with lower nocturnal PL levels. This is indeed what is observed in elder subjects, who have an increased number of awakenings and decreased amounts of non-REM stages, and in whom a dampening of the nocturnal rise is evident (van Coevorden et al., 1991). This diminished nocturnal rise in aging is associated with a decrease in the amplitude of the secretory pulses (Greenspan et al., 1990).

Studies in cats, rats and rabbits also indicate that PL may be one of the growth factors influencing sleep (Roky et al., 1995). It appears that its primary action as a sleep factor is to promote REM sleep. The effects of PL on sleep appear to be dependent on time of day, that is, PL promotes REM sleep only when administered during the normal rest period. The other biological actions of PL are numerous and include influences on osmoregulation, reproduction, growth, lactation, immune function and behavior.

C. The Present Invention

Typically, the age-associated decrease in GH and PL levels have been viewed merely as hormonal alterations resulting from decreased output by the pituitary. The present invention approaches this problem from a different point of view, namely, that aging causes the concomitant loss of quality sleep, GH and PL secretion. Put another way, if improved sleep patterns can be established, significant elevations in GH and PL levels may be achieved; moreover, this may be accomplished in a physiologic manner (i.e., without overdose toxicity). Conversely, if GH and PL levels can be stimulated during the night, the quality of sleep for aged individuals may be improved.

The present invention involves, in one aspect, the use of a particular drug to stimulate the secretion of GH and PL during sleep. In so doing, it is possible to improve sleep quality as measured by a decrease in wake time, an increase in SW and REM sleep, increase in sleep maintenance, increase in sleep efficiency, a decrease in sleep latency and normalization of distribution of SW and REM stages during the sleep period. Additional benefits may ensue, including improved cognitive abilities.

The designation for this compound is N-[1(R){[1,2-dihydro-1-methanesulfonylspiro-(3H-indole-3,4'-piperidine)-1'yl]carbonyl}-2-(phenylmethoxy)-ethyl]-2-amino-2-methylpropanamide methanesulfonate. Previously, this compound has been shown to have activity as a growth hormone and prolactin secretagogue, and has many properties in common with GHRP, another GH secretagogue. For example, its pituitary cell activity is antagonized by GHRP antagonist, and the response to a maximal dose of GHRP is not increased by further addition of the lead compound. The same cannot be said of GHRH, where one can increase GH secrease by adding the lead compound to cells treated with a maximal dose of GHRH.

D. Definitions

Elderly: Elderly is used in the context of the present invention as any individual exhibiting age-related alterations in sleep patterns. These effects usually are evident by about age 40, but may occur earlier in some individuals. It also may be useful to break down treatment of individuals based on age, for example, those persons aged 40, 45, 50, 55 and 60 and above. Average SWS for the young is about 75 to 125 min per night while for the elderly, the figure is about 0 to 50. Thus, adults with less that about 50 min per night SWS would qualify has having age-related sleep disorder.

Growth Hormone (GH): Growth hormone, also known as somatotropin, is a peptide hormone containing 191 amino acids and having a molecular weight of about 22 kD. It is secreted from the pituitary gland, stimulates the growth of all tissues that are capable of growing, increases protein synthesis, decreases glucose utilization, causes an increase in weight and length of the body, alters protein, carbohydrate, fat, bone and steroid metabolism and modulates immune function.

Growth Hormone Releasing Hormone (GHRH): Secreted from the hypothalamus, growth hormone releasing hormone (or factor) acts to increase the secretion of growth hormone by the pituitary gland. There is evidence that GHRH contributes to the regulation of sleep.

Growth Hormone Releasing Peptide (GHRP): Growth hormone releasing peptides are a family of peptide GH secretagogues. GHRP-6 has the sequence His-D-Trp-Ala-D-Phe-Lys-$NH_2$. GHRP-2 has the sequence D-Ala-D-β-Nal-Ala-Trp-D-Phe-Lys-$NH_2$. Nonpeptide GHRP's are being developed that have similar properties to peptide GHRP's. GHRP's also can synergize with GHRH to increase the secretion of GH.

The Drug: N-[1(R){[1,2-dihydro-1-methanesulfonylspiro-(3H-indole-3,4'-piperidine)-1'yl]carbonyl}-2-(phenylmethoxy)-ethyl]-2-amino-2-methylpropanamide methanesulfonate is a spiropiperidine that now has been shown to be capable of improving the quality of sleep (WO 94/13696). Because this drug has been shown to be a GH and secretagogue (Patchett et al., 1995), it is believed that the induction of GH secretion is at the basis of this drug's action on sleep, as well as its more recently discovered induction of PL secretion. The compound is synthesized as follows:

To a solution of 1.20 g (5.8 mmol) of 1'-methyl-1,2-dihydro-spiro[3H-indole-3,4'-piperidine] (Ong et al., 1983) in 20 ml of dry dichloromethane at 0° C. is added triethylamine (0.90 ml; 6.4 mmol) and methanesulfonyl chloride (0.49 ml; 6.35 mmol) and stirred for 30 min. The reaction mixture is poured into 15 ml of saturated aqueous sodium bicarbonate solution and extracted with dichloromethane (2×10 ml). The combined organics are washed with brine (20 ml), dried over anhydrous potassium carbonate, filtered and the solvent removed under pressure to yield 1.44 g of the methanesulfonamide derivative as pale yellow oil which is used without purification.

To a solution of the above crude product in 20 ml of dry 1,2-dichloromethane at 0° C. is added 1.0 ml (9.30 mmol) of 1-chloroethyl chloroformate, and then stirred at RT for 30 min and finally at reflux for 1 h. The reaction mixture is concentrated to approximately one-third of the volume and then diluted with 20 ml of dry methanol and refluxed for 1.5 h. The reaction is cooled to room temperature and concentrated to approximately one-half the volume. The precipitate is filtered and washed with a small volume of cold methanol. This yielded 1.0 g of the piperidine HCl salt as a white solid. The filtrate is concentrated and a small volume of methanol is added, followed by ether. The precipitated material is once again filtered, washed with cold ethanol, and dried. This provides an additional 0.49 g of the intermediate product 1,2-dihydro-1-methanesulfonylspiro-[3H-indole-3,4'-piperidine] hydrochloride.

To 0.35 g (1.15 mmol) of (2R)-2-[(1,1-dimethylethoxy)-carbonyl]amino-3-[2-(phenylmethyloxy)ethyl]-1-propanoic acid in 13 ml of dichloromethane is added the intermediate 1,2-dihydro-1-methanesulfonylspiro-[3H-indole-3,4'-piperidine]hydrochloride (0.325 g; 1.07 mmol), 0.18 ml (1.63 mmol) of N-methylmorpholine, 0.159 g (1.18 mmol) of 1-hydroxybenztriazole (HOBT) and stirred for 15 min. EDC (0.31 g; 1.62 mmol) is added and stirring continued for 1 h. An additional 60 μl of N-methylmorpholine is added and stirred for 45 min. The reaction mixture is poured into 5 ml of water and the organic layer separated. The organic layer is washed with 5 ml of 0.5N aqueous hydrochloric acid and 5 ml of saturated aqueous sodium bicarbonate solution. The combined organics are dried over anhydrous magnesium sulfate, and concentrated to yield 0.627 g of the product as a yellow foam which is used without purification.

To 0.627 g (1.07 mmol) of the above product in 5 ml of dichloromethane is added to 1.0 ml of trifluoroacetic acid and stirred at room temperature for 75 min. An additional 1.0 ml of trifluoroacetic acid is added and stirred for 10 min. The reaction mixture was concentrated, diluted with 5.0 ml of dichloromethane and carefully basified by pouring into 10 ml of 10% aqueous sodium carbonate solution. The organic layer is separated and the aqueous layer is further extracted with 2×15 ml of dichloromethane. The combined organics are washed with 5 ml of water, dried over potassium carbonate, filtered and concentrated to give the 0.486 of the amine as a light yellow foam which is used without purification.

To 0.486 g (1.01 mmol) of the amine and 10 ml of dichloromethane is added 0.26 g (1.28 mmol) of 2-[(1, 1-dimethyl-ethoxy)carbonyl]amino-2-methyl-propanoic acid, 0.173 g (1.28 mmol) of 1-hydroxybenztriazole (HOBT) and EDC (0.245 g; 1.28 mmol) and stirred overnight at room temperature. The reaction mixture was poured into 5.0 ml of water and the organic layer separated. The aqueous layer is back extracted with 5 ml of dichloromethane. The combined organics are washed with 5.0 ml of 0.5N aqueous hydrochloric acid, 5 ml of saturated aqueous sodium bicarbonate solution dried over anhydrous magnesium sulfate, and concentrated to yield 0.751 g of the crude product as a yellow foam. A solution of this crude product in dichloromethane is chromatographed on 25 g of silica gel and eluted with hexanesacetone/dichloromethane (70/25/5) and then hexanes/acetone/dichloromethane (65/30/5). This gives 0.63 g of the lead compound as a white solid.

Improvement in Sleep Quality: In determining whether a drug or treatment protocol achieves improvement of sleep quality, a number of different parameters are considered. For example, a decrease in wake time, an increase in SW and REM sleep, increase in sleep maintenance, increase in sleep efficiency, a decrease in sleep latency and normalization of distribution of SW and REM stages during sleep all are considered to be improvements in sleep quality. A drug or treatment protocol offering any of these to a subject would be considered to have improved the sleep quality of that patient. The methods by which one can determine improvement in sleep quality are described in the examples.

E. Active Ingredients

"Active Ingredients" according to the present invention are various forms of the drug. The chemical nomenclature for the compound is N-[1(R){[1,2-dihydro-1-methanesulfonylspiro-(3H-indole-3,4'-piperidine)-1'yl]carbonyl}-2-(phenylmethoxy)-ethyl]-2-amino-2-methylpropanamide methanesulfonate. This synthesis of this compound is set forth above. Prodrugs that are converted in vivo to the drug also are within the scope of the invention.

F. Pharmaceutical Compositions

Pharmaceutical compositions containing an active ingredient according to the present invention may be administered as pharmaceutically acceptable compositions that include physiologically acceptable carriers, buffers or other excipients. For example, pharmaceutical compositions may be administered in the form of injectable compositions either as liquid solutions or suspensions; solid forms suitable for solution or suspension in liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations which are suitable for oral administration are preferred. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

Typical dosages will be between 1.0 and 50.0 grams. Preferred dosages are 2.0 to 25.0 grams with 2.0, 5.0 and 25.0 grams being most preferred. Generally, one dose per night is administered just prior to retiring. Delayed release formulations are another embodiment of the present invention and may have somewhat greater or lesser total doses depending on the formulation.

G. Therapeutic Regimens

According to the present invention, the pharmaceutical composition is administered to subjects just prior to retiring. Typically, this will be within the last hour prior to retiring, but may be one-half hour or less prior to retiring. It also may be desirable to administer a second, or even a third dose during the normal sleep period. The administration may be via any common route including oral, nasal, buccal, rectal, vaginal, or topical. Alternatively, administration will be by intradermal subcutaneous, intramuscular, intraperitoneal, or intravenous injection. In a particular embodiment, the pharmaceutical composition is administered in a single oral dose formulation about one-half hour before retiring.

The term "unit dose" refers to physically discrete units suitable for use in humans, each unit containing a predetermined quantity of the pharmaceutical composition calculated to produce the desired response in association with its administration, i.e., the appropriate carrier, route and treatment regimen. The quantity to be administered, both according to number of treatments and unit dose, depends on the subject to be treated. Person having a greater or lesser reduction in growth hormone release will be given lesser or greater amounts, respectively, of the active ingredient. Precise amounts of the therapeutic composition also depend on the judgment of the practitioner and are peculiar to each individual.

VI. EXAMPLES

A. Subjects and Methods

Young subjects: Nine healthy young men, ages 18–30 years (mean±SD:27±3 years), without sleep complaint, participated in the study. All were non-smokers and did not take any other drug. The body mass index averaged 22.3±2.7 kg/m$^2$.

The protocol was designed as a double blind, placebo-controlled, three-period cross-over study. Each subject participated in three treatment periods, presented in random (latin square) order, and separated by at least 14 days. Each period involved administration of the drug N-[1(R){[1,2-dihydro-1-methanesulfonylspiro-(3H-indole-3,4'-piperidine)-1'yl]carbonyl}-2-(phenylmethoxy)-ethyl]-2-amino-2-methylpropanamide methanesulfonate as a single oral dose at bedtime, around 2245 h, for seven consecutive days. Doses were 5 mg and 25 mg of the drug and matching placebo.

All subjects spent an habituation night in the sleep laboratory prior to the beginning of the study. Throughout the entire study, the subjects were asked to maintain regular sleep-wake cycles (bedtimes 2300 h–0700 h in total darkness). On day 6 of each period, they were required to report at 1900 h to the sleep laboratory for a reacclimatation night. They were discharged in the morning of day 7 and re-admitted between 1600 h and 1700 h the same day. At 1700 h, a catheter was inserted into a forearm vein and 1 ml blood samples were obtained at 15-min intervals for 25 consecutive hours starting at 1800 h. During both nights, bedtimes were 2300 h–0700 h in total darkness and sleep was polygraphically recorded. Snacks between meals, alcoholic beverages, daytime recumbency and naps were prohibited. All studies were performed in the Sleep Laboratory of the Center for the Study of Biological Rhythms (CERB) of Erasme Hospital, Université Libre de Bruxelles (Brussels, Belgium). All recordings were scored by the same experienced polysomnographist who was blind to the study condition. The protocol was approved by the Institutional Review Board and all subjects gave written informed consent after receiving a complete explanation of the aims and means of the study.

Older adults: Six healthy, fully self-sufficient older subjects (4 men, 2 women), ages 65–71 years, with a body mass index averaging 24.1±1.5 kg/m$^2$, were included in the study. None had sleep complaints. These subjects were part of a placebo-controlled, randomized study, involving two medical centers and a total of 16 subjects, on the effects of prolonged treatment with the drug on somatotropic function. Sleep was recorded only in one of the centers which enrolled six volunteers on the drug and one volunteer on placebo. The subjects were non-smokers and did not take any drug. They all spent an habituation night in the sleep laboratory prior to the beginning of the study. They each participated in two successive treatment periods separated by a 14-day washout period. Each treatment period involved administration of the drug as a single oral dose between 2200 h and 2300 h for 14 consecutive days. Doses were 2 mg during the first treatment period and 25 mg for the second treatment period. Sleep was polygraphically recorded for two consecutive nights at baseline (i.e., before the beginning of the first treatment period) and at the end of each treatment period. On each occasion, a catheter was inserted into a forearm vein at 0700 h immediately after the first night, and 1 ml blood samples were obtained at 20-min intervals for 25 consecutive hours. During both nights, bedtimes were 2300 h–0700 h in total darkness. Snacks between meals, alcoholic beverages, daytime recumbency and naps were prohibited. All studies were performed in the Clinical Research Center of the University of Chicago (Chicago, Ill.). All recordings were scored by the same experienced polysomnographist who was blind to the study condition. The protocol was approved by the Institutional Review Board and all subjects gave written informed consent after receiving a complete explanation of the aims and means of the study.

Sleep recording and analysis: Polygraphic sleep recordings were scored in stages wake, I, II, III, IV and rapid-eye-movement (REM) using standardized criteria (Rechtschaffen & Kales, 1968). Sleep onset and final morning awakening were defined as, respectively, the times of the first and last epoch scored II, III, IV or REM. SW sleep was defined as stages III and IV. The sleep period was defined as the time interval separating sleep onset from final morning awakening. Sleep efficiency was calculated as the total recording time minus the time spent awake, expressed in percent of the total recording time. Sleep maintenance was calculated as the sleep period minus the total duration of awakenings, expressed in percent of the sleep period. Sleep latency was defined as the time interval separating lights off from sleep onset. REM latency was defined as the time interval separating sleep onset from the first epoch scored REM.

Statistical methods: In each group of subjects, all comparisons between placebo (or baseline), low dose and high dose were performed by ANOVA for repeated measures with pairwise contrasts tested by the Fisher procedure. The primary output measures targeted for analysis were: sleep period, sleep latency, sleep efficiency, sleep maintenance, amounts of wake, stages I+II, stage III, stage IV, stage REM and REM latency. All statistical calculations were performed using the Statview$^{SE+}$ software for Macintosh (Abacus Concepts, Berkeley, Calif.). Unless otherwise stated, all results are expressed as the mean±SEM.

B. Results

Young subjects: Polygraphic sleep recordings of sufficient quality for reliable scoring were obtained during 20 of the 27 reacclimatation nights (only 4 subjects had valid recordings during all 3 nights) and 26 of the 27 nights with blood sampling. Therefore, statistical calculations could only be performed for the nights with blood sampling and involved 8 of the 9 subjects. Table 1 summarizes the mean values for all calculated sleep parameters in the three conditions. All parameters were similar in the placebo and low dose (5 mg) conditions. Following high dose (25 mg) treatment, the duration of stage IV was nearly 50% higher (p<0.05) and the amount of REM sleep was more than 20% higher (p<0.05) than after placebo treatment. These increases in stages IV and REM reflected a nonsignificant trend towards lesser amounts of wake (which decreased, on average, by 34% as compared to the placebo condition). The sleep period and the amounts of stages I+II and III were similar across the three treatment conditions.

TABLE 1

SLEEP PARAMETERS IN YOUNG SUBJECTS DURING NIGHTS WITH BLOOD SAMPLING

|  | Placebo | Low Dose | High Dose |
|---|---|---|---|
| Sleep period (min) | 446 ± 6 | 449 ± 7 | 455 ± 7 |
| Sleep latency (min) | 39 ± 7 | 36 ± 8 | 28 ± 6 |
| Sleep efficiency (%) | 78 ± 4 | 78 ± 3 | 84 ± 2 |
| Sleep maintenance (%) | 83 ± 4 | 83 ± 3 | 89 ± 2 |
| Amount of wake (min) | 77 ± 16 | 76 ± 12 | 52 ± 10 |
| Amount of stage I+II (min) | 208 ± 18 | 216 ± 13 | 214 ± 13 |
| Amount of stage III (min) | 38 ± 5 | 31 ± 5 | 34 ± 4 |
| Amount of stage IV (min) | 37 ± 7 | 43 ± 9 | 54 ± 10* |
| Amount of REM (min) | 85 ± 7 | 83 ± 8 | 103 ± 3* |
| REM latency (min) | 97 ± 20 | 94 ± 19 | 67 ± 4 |

\* - p<0.05 as compared to placebo
n = 8
Mean ± SEM

The cumulative profiles of wake, stage IV and REM, shown in FIG. 1, indicate that the effects of high dose treatment on stage IV and on wake were mostly apparent during the beginning of the night whereas the increase in REM stage occurred around the middle of the sleep period.

To further analyze the effects of the drug, the number of deviations from "normal" sleep was recorded for each treatment condition. Based on previous analyses of sleep in normal young subjects sleeping in the laboratory (Linkowski et al., 1989; Copinschi et al., 1990; Carskadon & Dement, 1994), the following arbitrary criteria for "normal" sleep were defined: sleep maintenance ≧85%; sleep latency≦45 min; REM latency 40–100 min; SW stages≧75 min; REM stages≧90 min; majority of SW stages occurring during the first 3rd of the sleep period. As shown in FIG. 2, deviations from "normal" sleep (which presumably represented deleterious effects of the sampling catheter) were present in a large proportion of individual profiles under placebo, as well as under the low dose treatment, but in very few of the profiles under the high dose treatment. Since the six criteria for "normal" sleep are not mutually dependent, i.e., each deviation may occur in the absence of any other deviation, it was not possible to calculate for each treatment condition the global frequency of deviations. The frequency of deviations averaged 42%, 44% and 8% under placebo, low dose and high dose, respectively. The difference between high dose and the other two conditions was statistically significant (p<0.03).

The apparent frequency of low-amplitude GH pulses was increased with both low and high doses of the drug as compared with placebo, but no significant elevation of overall GH secretion over the 24 h span was observed. However, plasma levels of insulin-like growth factor I (IGF-I) were increased with both dosages of the drug in a dose-dependent manner. Correlation analyses failed to demonstrate significant associations between improvements of sleep parameters and increases in GH pulsatility or IGF-I levels.

Older adults: Valid polygraphic sleep recordings were obtained during all the reacclimatation nights (i.e., without blood sampling) and in 17 of the 18 nights with blood sampling. Therefore, statistical calculations were performed for all subjects for the nights without blood sampling and for 5 of 6 subjects for the nights with blood sampling (Table 2). Under baseline conditions, the age-related alterations of sleep quality which characterize the elderly population (increased amounts of wake, decreased amounts of stages IV and REM; (Bliwise, 1994)) were observed, even though none of the subjects had subjective sleep complaints. A significant increase in the duration of REM stage under the treatment with the low dose (2 mg) as compared to baseline (p<0.05) was observed during the nights without blood sampling. This increase in REM sleep occurred in 5 of the 6 subjects and these same 5 subjects also demonstrated an increase in REM sleep following high dose treatment. However, for the high dose (25 mg) treatment, the increase in REM sleep failed to reach significance at the group level because of a significantly (p<0.02) outlying value contributed by the non-responder subject. On average, including the nights with and without blood sampling, the amount of REM sleep in the 5 responders was 40±9 min at baseline, 65±8 min after low dose and 63±7 min after high dose. During the nights with blood sampling, REM latency was decreased following low dose treatment, as compared to baseline conditions (p<0.02), and a similar trend occurred following high dose treatment. No other significant effect of the treatment could be evidenced on any single sleep parameter.

TABLE 2

SLEEP PARAMETERS IN OLDER SUBJECTS DURING NIGHTS WITH AND WITHOUT BLOOD SAMPLING

|  | Placebo | Low Dose | High Dose |
|---|---|---|---|
| Without Blood Sampling |  |  |  |
| Sleep period (min) | 425 ± 18 | 425 ± 15 | 423 ± 10 |
| Sleep latency (min) | 38 ± 16 | 26 ± 11 | 27 ± 9 |
| Sleep efficiency (%) | 67 ± 6 | 73 ± 5 | 70 ± 5 |
| Sleep maintenance (%) | 75 ± 5 | 82 ± 4 | 80 ± 5 |
| Amount of wake (min) | 105 ± 23 | 74 ± 14 | 85 ± 20 |
| Amount of stage I+II (min) | 188 ± 10 | 204 ± 28 | 201 ± 22 |
| Amount of stage III (min) | 52 ± 12 | 51 ± 3 | 37 ± 6 |
| Amount of stage IV (min) | 31 ± 15 | 25 ± 14 | 36 ± 18 |
| Amount of REM (min) | 50 ± 10 | 72 ± 9* | 63 ± 12 |
| REM latency (min) | 103 ± 24 | 95 ± 14 | 90 ± 12 |
| With Blood Sampling |  |  |  |
| Sleep period (min) | 450 ± 9 | 413 ± 16 | 400 ± 23 |
| Sleep latency (min) | 26 ± 9 | 35 ± 12 | 29 ± 14 |
| Sleep efficiency (%) | 57 ± 4 | 62 ± 7 | 59 ± 7 |
| Sleep maintenance (%) | 61 ± 5 | 73 ± 9 | 71 ± 7 |
| Amount of wake (min) | 178 ± 21 | 115 ± 39 | 117 ± 27 |
| Amount of stage I+II (min) | 180 ± 14 | 170 ± 25 | 185 ± 14 |
| Amount of stage III (min) | 31 ± 7 | 47 ± 18 | 36 ± 14 |
| Amount of stage IV (min) | 28 ± 8 | 31 ± 10 | 21 ± 10 |
| Amount of REM (min) | 33 ± 12 | 50 ± 10 | 48 ± 7 |
| REM latency (min) | 228 ± 43 | 72 ± 8** | 122 ± 22 |

\* - p<0.05 as compared to baseline
\*\* - p<0.02 as compared to baseline
n = 6 (top) and 5 (bottom)
Mean ± SEM For both nights, the percentage of deviations from "normal" sleep was recorded for each treatment condition, using the same criteria as for young subjects, except for sleep maintenance (normal values ≧80%), amount of REM stages (≧60 min) and amount of SW stages (60 min without and 45 min with blood sampling), consistent with the well-known effects of age on sleep quality (Bliwise, 1994). During the nights without blood sampling, the frequency of deviations averaged 44%, 28% and 36% under placebo, low dose and high dose, respectively. The difference between low dose treatment and baseline conditions approached statistical significance (p<0.09). During the nights with blood sampling, the frequency was 63%, 33% and 63% under baseline, low dose and high dose, respectively. The difference between low dose and the other two conditions was statistically significant (p<0.02).

Plasma levels of GH over the 24-hour span were increased with the 25 mg dosage as compared to baseline, primarily because of an enhancement of the low-amplitude pulses, and IGF-I values were increased by approximately 50%. Treatment with 2 mg of the drug did not affect GH levels, GH pulsatility or IGF-I levels.

C. Discussion

This placebo-controlled study in normal young men demonstrates that prolonged treatment with the drug, a compound developed as an orally active GH secretagogue mimicking the effects of GHRP, improves sleep quality. Indeed, treatment with the drug minimized the perturbations of sleep quality associated with the presence of a catheter for venous blood sampling throughout the night. Additionally, data obtained in a small group of healthy elderly adults before and after two periods of treatment with low and high dose, respectively, suggest that the drug may alleviate alterations of sleep which normally occur in old age. Indeed, an increase in the amount of REM sleep, averaging approximately 50%, was observed following both low and high dose treatment. The apparent decrease in the number of sleep disturbances which, paradoxically, was observed following low dose but not high dose treatment, will need to be confirmed.

These findings suggest that prolonged treatment with a compound which is able to induce elevations of GH, prolactin and/or IGF-I levels within the physiological range may also improve sleep quality. The mechanisms of action of the drug are not fully understood, but several lines of evidence indicate that the compound acts on the hypothalamus (Bowers, 1994). Thus, the effects of the drug on sleep quality could reflect a direct central nervous system action of the drug. Alternatively, these somnogenic effects could be mediated by the peripheral hormonal changes induced by the treatment, i.e., increased GH pulsatility and elevations of IGF-I levels. The findings in older adults, and the apparent absence of correlation between hormonal and sleep effects in the young subjects, do not support this latter hypothesis. Because of the putative role of REM sleep in cognitive function and particularly in memory retention (Bonnet, 1994), an enhancement of REM sleep may have additional functional benefits in older adults.

REFERENCES

The following references, to the extent that they provide exemplary procedural or other details supplementary to those set forth herein, are specifically incorporated herein by reference:

Bliwise, In: PRINCIPLES AND PRACTICE OF SLEEP MEDICINE, Kryger, Roth, Dement (eds). W. B. Saunders, Philadelphia, Pa. p. 26–39, 1994.
Bonnet, In: PRINCIPLES AND PRACTICE OF SLEEP MEDICINE, Kryger, Roth, Dement (eds). W. B. Saunders, Philadelphia, Pa. p. 50–67, 1994.
Born, Muth et al., Psychoneuroendocrinolog 13: p. 233–243, 1988.
Bowers, J. Clin. Endocrinol. Metab. 79: p. 940–942, 1994.
Carskadon & Demen, In: PRINCIPLES AND PRACTICE OF SLEEP MEDICINE. Kryger, Roth, Dement (eds). W. B. Saunders, Philadelphia, Pa. p. 16–25, 1994.
Copinschi et al, Sleep 13: p. 232–244, 1990.
Copinschi & Van Cauter, Hormone Res. 43: p. 20–24, 1995.
Degerblad, Almkvist et al., Acta Endocrinol 123: p. 185–193, 1990.
Desir et al., J. Clin. Endocrinol. 55: p. 849–857, 1982.
Ehlers, Reed et al., Neuroendocrinology 42: p. 467–474, 1986.
Finkelstein, Roffwarg et al., J. Clin. Endocrinol Metab. 35: p. 665–670, 1972.
Gaillard, In: PRINCIPLES AND PRACTICE OF SLEEP MEDICINE. Kryger, Roth, Dement (eds). W. B. Saunders, Philadelphia, Pa. p. 349–354, 1994.
Garry, Roussel et al., Acta Endocrinol 110: p. 158–163, 1985.
Golstein, Van Cauter et al., J. Clin. Endocrinol Metab. 56: p. 433–440, 1983.
Greenspan et al., Am. J. Physiol. 258: p. E799–E804, 1990.
Ho, Evans et al., J. Clin. Endocrinol Metab. 64: p. 51–58, 1987.
Holl, J. Clin. Endocrinol. Metab. 72: p. 854–861, 1991.
Iranmanesh, Lizarralde et al., J. Clin. Endocrinol. Metab. 73: p. 1081–1088, 1991.
Iranmanesh, Lizarralde et al., J. Clin. Endocrinol. Metab. 72: p. 108–115, 1991.
Jarret, Greenhouse et al., Biol. Psychiatry 27: p. 497–509, 1990. Kerkhofs, Van Cauter et al., Am. J. Physiol. 264: p. E592–E598, 1993.
Lang, Schernthaner et al., J. Clin. Endocrinol. Metab. 65: p. 535–540, 1987.
Linkowski et al., Electroenceph. Clin. Neurophysiol. 73: p. 279–284, 1989.
Mamelak et al., Sleep 9: p. 285–289, 1986.
McCauley, G. A., Acta Paediatr Scand (suppl) 356: p. 70–72, 1989.
McCracken, Poland et al., J. Clin. Endocrinol Metab. 72: p. 90–95, 1991.
Mendelson et al., Biol. Psychiatry 15: p. 613–618, 1980.
Mendelson, HUMAN SLEEP: RESEARCH AND CLINICAL CARE. Plenum Press, New York. p. 436, 1987.
Obál, Alfodi et al., Am. J. Physiol. 255: p. R310–R316, 1988.
Obál, Payne et al., Sleep Res. 20A: p. 192, 1991a.
Obál, Payne et al., Brain Res. 557: p. 149–153 1991b.
Ong et al., J. Med. Chem. 23: p. 981–986, 1983.
Oyama and Takiguchi, Travail recu lo, 6: p. 289–297, Japan 1970.
Patchett et al., Proc. Nat'l Acad. Sci. USA 92: p. 7001–7005, 1995.
Prinz, Weitzman et al., J. Gerontol. 38: p. 519–524, 1983.
Prinz, J. Clin. Neurophysiol. 12: p. 139–146, 1995.
Rechtschaffen & Kales, Government Printing Office, Washington, D.C., 1968.
Roky et al., Sleep 18: p. 536–542, 1995.
Sassin, Parker et al., Science. 165: p. 513–515, 1969.
Scharf et al., The Journal of Clinical Psychiatry 46: p. 222–225, 1985.
Shibasaki, Shizume et al., J. Clin. Endocrinol. Metab. 58: p. 212–214, 1984.
Steiger, Herth et al., Acta Endocrinol (Copenh.), 116: p.36–42, 1987.
Steiger, Guldner et al., Sleep Res. 20A: p. 195, 1991.
Steiger et al., Neuroendocrinology 56: p. 566–573, 1992.
Takahara et al., J. Clin. Endocrinol Metab. 44: p. 1014–1017, 1977.
Takahashi et al., J. Clin. Invest. 47: p. 2079–2090, 1968.
Van Cauter et al., J. Endocrinol. Invest. 8: p. 381–391, 1985.
Van Cauter et al., FIRST MEETING OF THE SOCIETY FOR RESEARCH ON BIOLOGICAL RHYTHMS, Jacksonville, Fla., #18, 1988.
Van Cauter, Kerkhofs et al., Arch. Gen. Psychiatry 48: p. 348–356, 1991.
Van Cauter, Kerkhofs et al., J. Clin. Endocrinol Metab. 74: p. 1441–1450, 1992.
Van Cauter, Caufriez et al., J. Clin. Endocrinol Metab. 74: p. 1451–1459, 1992.

van Coevorden, Mockel et al., *American Physiological Society*, 91: p. 0193–1849, E651–E661, 1991.

Vermeulen, A., *J. Clin. Endocrinol. Metab.* 64: p. 884–888, 1987.

Vickers, *International Anesthesiology Clinics* 7: p. 75–89, 1967.

WO 94/13696.

What is claimed is:

1. A method for improving the sleep quality of a subject comprising:
   (a) identifying a subject having a hormonally-related sleep disorder; and
   (b) administering to said subject an amount of N-[1(R){[1,2-dihydro-1-methanesulfonylspiro-(3H-indole-3,4'-piperidine)-1'yl]carbonyl}-2-(phenyl methoxy)-ethyl]-2-amino-2-methylpropanamide methanesulfonate effective to improve the sleep quality of said subject.

2. The method of claim 1, wherein said subject is at least about 40 years of age.

3. The method of claim 2, wherein said subject is at least about 50 years of age.

4. The method of claim 3, wherein said subject is at least about 60 years of age.

5. The method of claim 1, wherein the effective amount is between about 1.0 to 50.0 mg.

6. The method of claim 5, wherein the effective amount is about 5.0 mg.

7. The method of claim 1, wherein said subject has diminished levels of growth hormone or prolactin.

8. The method of claim 1, wherein said subject has diminished levels of growth hormone and prolactin.

9. The method of claim 1, wherein said administration is oral.

10. The method of claim 1, wherein said administration occurs within one hour prior to retiring.

11. The method of claim 10, wherein said administration occurs within one-half hour prior to retiring.

12. The method of claim 1, wherein said N-[1(R){[1,2-dihydro-1-methanesulfonylspiro-(3H-indole-3,4'-piperidine)-1'yl]carbonyl}-2-(phenylmethoxy)-ethyl]-2-amino-2-methylpropanamide methanesulfonate is provided in a slow release formulation.

* * * * *